United States Patent
Ritzeler et al.

(10) Patent No.: US 9,067,918 B2
(45) Date of Patent: Jun. 30, 2015

(54) CRYSTALLINE FORMS OF 2-(2-METHYL-AMINO-PYRIMIDIN-4-YL)-1H-INDOLE-5-CARBOXYLIC ACID [(S)-1-CARBAMOYL-2-(PHENYL-PYRIMIDIN-2-YL-AMINO)-ETHYL]-AMIDE

(71) Applicant: Sanofi, Paris (FR)

(72) Inventors: Olaf Ritzeler, Frankfurt am Main (DE); Mandy Mohnicke, Frankfurt am Main (DE); Guenter Billen, Frankfurt am Main (DE); Bruno Baumgartner, Frankfurt am Main (DE); Martin Brockelmann, Frankfurt am Main (DE); Norbert Nagel, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/363,146

(22) PCT Filed: Dec. 4, 2012

(86) PCT No.: PCT/EP2012/074339
§ 371 (c)(1),
(2) Date: Jun. 5, 2014

(87) PCT Pub. No.: WO2013/083553
PCT Pub. Date: Jun. 13, 2013

(65) Prior Publication Data
US 2014/0336211 A1    Nov. 13, 2014

(30) Foreign Application Priority Data

Dec. 6, 2011    (EP) ..................... 11306618

(51) Int. Cl.
*A01N 43/54*    (2006.01)
*A61K 31/505*    (2006.01)
*C07D 403/12*    (2006.01)
*A61K 31/506*    (2006.01)
*C07D 403/14*    (2006.01)

(52) U.S. Cl.
CPC ............ *C07D 403/12* (2013.01); *A61K 31/506* (2013.01); *C07D 403/14* (2013.01)

(58) Field of Classification Search
CPC .............................. C07D 403/14; A61K 31/506
See application file for complete search history.

(56) References Cited

U.S. PATENT DOCUMENTS

| | | | | |
|---|---|---|---|---|
| 7,285,560 B2 * | 10/2007 | Ritzeler et al. | ............... | 514/275 |
| 7,462,638 B2 | 12/2008 | Michaelis et al. | | |
| 8,778,955 B2 * | 7/2014 | Ritzeler et al. | ............... | 514/275 |
| 8,809,358 B2 * | 8/2014 | Michaelis et al. | ........... | 514/275 |
| 2007/0244139 A1 * | 10/2007 | Ritzeler et al. | ............... | 514/275 |
| 2008/0214813 A1 | 9/2008 | Graeser et al. | | |

FOREIGN PATENT DOCUMENTS

| | | |
|---|---|---|
| WO | 2004022057 A1 | 3/2004 |
| WO | 2004022553 A1 | 3/2004 |
| WO | WO 2004022057 A1 * | 3/2004 |
| WO | WO 2004022553 A1 * | 3/2004 |
| WO | 2006128585 A1 | 12/2006 |
| WO | 2012019967 A1 | 2/2012 |

OTHER PUBLICATIONS

J. Lee et al., 148 British Journal of Pharmacology, 366-375 (2006).*
K. Ziegelbauer et al., 145 British Journal of Pharmacology, 178-192 (2005).*
G. Mbalaviele et al., 329 The Journal of Pharmacology and Experimental Therapeutics, 14-25 (2009).*
S. Dai, et al., 279 The Journal of Biological Chemistry, 37219-37222 (2004).*
R.F. Schwabe et al., 290 American Journal of Physiology—Gastrointestinal and Liver Physiology (2006).*
E. Niederberger et al., 22 The FASEB Journal, 3432-3442 (2008).*
P. Coish et al., 16 Expert Opinion on Therapeutic Patents, 1-12 (2006).*
M. Karin et al., 3 Nature Reviews Drug Discovery, 17-26 (2004).*
I.E. Tchivileva, 5 Molecular Pain (2009).*
Preformulation in Solid Dosage Form Development at 239-240 (M. C. Adeyeye et al., eds., 2008).*
Solid State Characterization of Pharmaceuticals 427-450 (R.A. Storey et al., eds., 2011).*
Byrn, S., Pfeiffer, R., Ganey, M., Hoiberg, C., Poochikian, G., "Pharmaceutical Solids: A Strategic Approach to Regulatory Considerations"; Pharmaceutical Research, vol. 12, No. 7, (Month Day, 1995).
European Search Report for European Patent Application No. EP 11 30 6618 dated Mar. 13, 2012 (mailed Mar. 20, 2012).

* cited by examiner

*Primary Examiner* — Alexander R Pagano
(74) *Attorney, Agent, or Firm* — McDonnell Boehnen Hulbert & Berghoff LLP

(57) ABSTRACT

The present invention relates to polymorphs and hydrates of 2-(2-methylamino-pyrimidin-4-yl)-1H-indole-5-carboxylic acid [(S)-1-carbamoyl-2-(phenyl-pyrimidin-2-yl-amino)-ethyl]-amide, processes for their preparation and their use, in particular in pharmaceutical compositions.

20 Claims, 5 Drawing Sheets

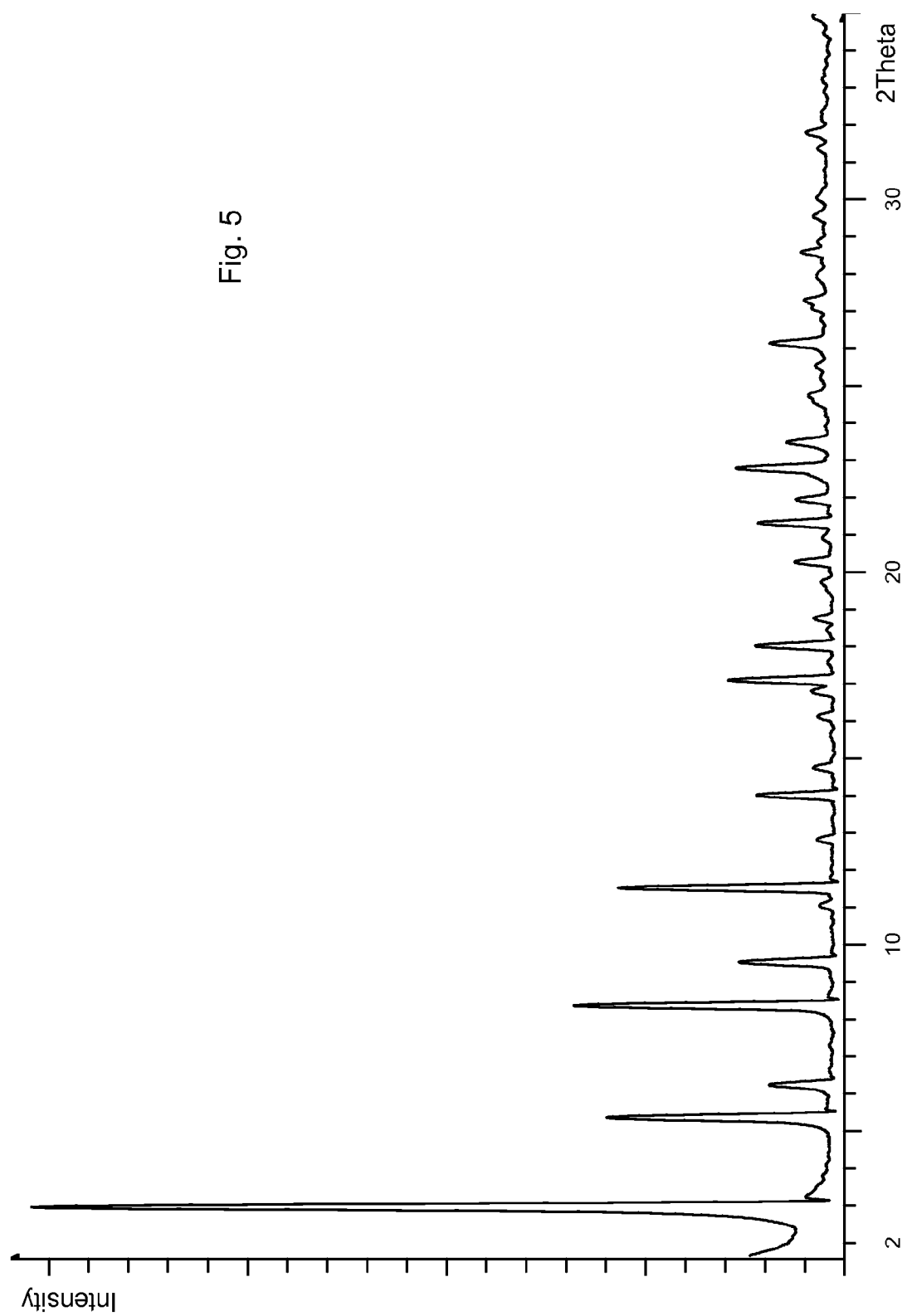

CRYSTALLINE FORMS OF 2-(2-METHYL-AMINO-PYRIMIDIN-4-YL)-1H-INDOLE-5-CARBOXYLIC ACID [(S)-1-CARBAMOYL-2-(PHENYL-PYRIMIDIN-2-YL-AMINO)-ETHYL]-AMIDE

This application is a national stage application under 35 U.S.C. § 371 of International Application No. PCT/EP2012/074339, filed Dec. 4, 2012, the disclosure of which is explicitly incorporated by reference herein.

The present invention relates to polymorphs and hydrates of 2-(2-methylamino-pyrimidin-4-yl)-1H-indole-5-carboxylic acid [(S)-1-carbamoyl-2-(phenyl-pyrimidin-2-yl-amino)-ethyl]-amide, processes for their preparation and their use, in particular in pharmaceutical compositions.

2-(2-Methylamino-pyrimidin-4-yl)-1H-indole-5-carboxylic acid [(S)-1-carbamoyl-2-(phenyl-pyrimidin-2-yl-amino)-ethyl]-amide of the formula I,

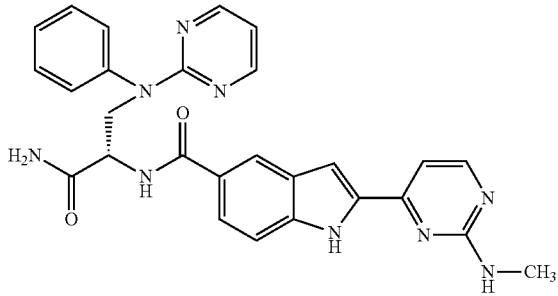

I which is also abbreviated herein as "compound I", is a pharmaceutical active compound which inhibits IκB kinase (I-kappa-B kinase, IKK) and is useful for the treatment of various diseases such as osteoarthritis or pain, for example, as is described in WO 2004/022553, U.S. Pat. No. 7,285,560, WO 2004/022057 and U.S. Pat. No. 7,462,638, for example. However, data concerning crystalline forms, polymorphs or hydrates of 2-(2-methylamino-pyrimidin-4-yl)-1H-indole-5-carboxylic acid [(S)-1-carbamoyl-2-(phenyl-pyrimidin-2-yl-amino)-ethyl]-amide are not disclosed in the prior art.

Polymorphism is the ability of a compound to exist in more than one crystalline form or crystal structure. Different polymorphs represent distinct solids sharing the same molecular formula, yet each polymorph may have distinct physical properties. A specific compound may give rise to a variety of polymorphic forms wherein each form has different and distinct physical properties, such as different solubility profiles, different thermodynamic stability, different crystallization behavior, different filterability, different melting point temperatures and/or different X-ray diffraction patterns. The difference in the physical properties of different polymorphic forms results from different orientation and intermolecular interactions of adjacent molecules in the solid. Polymorphic forms of a compound can be distinguished by X-ray diffraction and by other methods such as infrared spectroscopy or Raman spectroscopy, for example. These statements apply likewise to hydrates, i.e. solid addition compounds of a compound with water, which are a specific form of solvates and which may form when a compound is in contact with water, for example when crystallizing a compound in the presence of water.

However, as acknowledged by the person skilled in the art, the presence of different crystalline polymorphic forms or hydrates of a compound cannot be foreseen. Neither the existence of polymorphic forms or hydrates nor the number of polymorphic forms or hydrates can be foreseen. Also the conditions under which crystallization takes place to give a specific form, and the characteristics of the polymorphic forms and hydrates cannot be predicted. Since properties such as the solubility and stability and consequently the suitability for use and storage of each polymorphic form and hydrate may vary, identifying the existence of polymorphic forms and solvates such as hydrates is essential for providing pharmaceuticals with increased storage stability or suitable solubility profiles, for example. Thus, it is desirable to investigate all solid state forms of a drug substance, including polymorphic forms and hydrates.

Accordingly, it was the object of the present invention to provide solid forms of 2-(2-methylamino-pyrimidin-4-yl)-1H-indole-5-carboxylic acid [(S)-1-carbamoyl-2-(phenyl-pyrimidin-2-yl-amino)-ethyl]-amide, in particular forms which have a favorable property profile or are useful in the preparation of the compound. This object was attained by providing polymorphs and hydrates which are selected from the series consisting of polymorph 1, polymorph 2, polymorph 3, hydrate 1 and hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide and any mixture thereof, which polymorphs and hydrates have favorable properties with respect to stability, solubility, processability, hygroscopicity, flowability, filterability or crystallization rate, for example, wherein polymorph 1, polymorph 2, polymorph 3, hydrate 1 and hydrate 2 may be characterized by any of their data given herein. The data used to characterize the polymorph and hydrates of the present invention were obtained as described below. In the context of the present invention, polymorph, polymorphic form, hydrate etc. refers to a polymorph, polymorphic form or hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide. Terms like "polymorph", "polymorphic form", "phase" and "crystalline phase" may be used interchangeably herein.

One embodiment of the present invention relates to a crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide which is selected from the series consisting of polymorph 1, polymorph 2, polymorph 3 and any mixture thereof, wherein polymorph 1, polymorph 2 and polymorph 3 may be characterized by any of their data given herein. One embodiment of the present invention relates to a crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide which is selected from the series consisting of hydrate 1 and hydrate 2 and any mixture thereof, wherein hydrate 1 and hydrate 2 may be characterized by any of their data given herein.

One embodiment of the present invention relates to polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using $CuK_{\alpha 1}$ (CuK-alpha1) radiation in reflection mode at 2Theta (2θ) angles in degree [°] of 14.9±0.2, 19.4±0.2, 19.7±0.2, 20.0±0.2, 22.3±0.2, 25.0±0.2.

One embodiment of the present invention relates to polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha1}$ (CuK-alpha1) radiation in reflection mode at 2Theta (2θ) angles in degree [°] of 10.4±0.2, 14.9±0.2, 17.5°±0.2, 18.0±0.2, 19.4±0.2, 19.7±0.2, 20.0±0.2, 21.0±0.2, 22.3±0.2, 25.0±0.2.

One embodiment of the present invention relates to polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has any one or more of the characteristic reflections in an X-ray powder diffractogram using CuK$_{\alpha1}$ radiation in reflection mode which are given above or below herein.

One embodiment of the present invention relates to polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has an X-ray powder diffraction pattern substantially as the one shown in FIG. 1 which has been obtained using CuK$_{\alpha1}$ radiation in reflection mode, wherein the exact relative intensities of the reflections depicted in FIG. 1 are not a prerequisite, but may vary and represent another embodiment of the invention.

Polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide may also be characterized by its melting characteristics such as its melting point determined by differential scanning calorimetry (DSC) with an onset temperature of 253±1° C. and/or a peak temperature of 257±1° C. (heating rate 10° C./minute).

Polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide is the thermodynamically most stable polymorph of 2-(2-methylamino-pyrimidin-4-yl)-1H-indole-5-carboxylic acid [(S)-1-carbamoyl-2-(phenyl-pyrimidin-2-yl-amino)ethyl]-amide at temperatures above about 20° C., as is confirmed in phase conversion experiments, for example. Therefore, in comparison to the other polymorphs, polymorph 1 is particularly suitable when a high stability is desired. Polymorph 1 is further characterized by a low hygroscopicity of about 0.9% water uptake at a high relative humidity of 80%. In view of its stability and low hygroscopicity, polymorph 1 is particularly suitable for storage of 2-(2-methylamino-pyrimidin-4-yl)-1H-indole-5-carboxylic acid [(S)-1-carbamoyl-2-(phenyl-pyrimidin-2-yl-amino)-ethyl]-amide. Polymorph 1 is further characterized by a low solubility in water, which allows an easy realization of a depot effect with respect to the pharmacological activity of 2-(2-methylamino-pyrimidin-4-yl)-1H-indole-5-carboxylic acid [(S)-1-carbamoyl-2-(phenyl-pyrimidin-2-yl-amino)-ethyl]-amide by administering a suitable pharmaceutical formulation containing solid polymorph 1. Therefore, polymorph 1 is particularly suitable for use in pharmaceutical compositions, or in medicaments, which are designed to have a long duration of action.

One embodiment of the present invention relates to polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha1}$ (CuK-alpha1) radiation in reflection mode at 2Theta (2θ) angles in degree [°] of 5.8±0.2, 6.7±0.2, 9.3±0.2, 11.2±0.2, 19.4±0.2, 22.1±0.2.

One embodiment of the present invention relates to polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha1}$ (CuK-alpha1) radiation in reflection mode at 2Theta (2θ) angles in degree [°] of 5.8±0.2, 6.7±0.2, 9.3±0.2, 9.9±0.2, 11.2±0.2, 16.5±0.2, 18.1±0.2, 19.4±0.2, 22.1±0.2.

One embodiment of the present invention relates to polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has any one or more of the characteristic reflections in an X-ray powder diffractogram using CuK$_{\alpha1}$ radiation in reflection mode which are given above or below herein.

One embodiment of the present invention relates to polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has an X-ray powder diffraction pattern substantially as the one shown in FIG. 2 which has been obtained using CuK$_{\alpha1}$ radiation in reflection mode, wherein the exact relative intensities of the reflections depicted in FIG. 2 are not a prerequisite, but may vary and represent another embodiment of the invention.

Polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide may also be characterized by its behavior in differential scanning calorimetry (DSC), where it gives rise to an endothermic peak with an onset temperature of 222±1° C. and/or a peak temperature of 225±1° C., followed by an endothermic peak with an onset temperature of 248±1° C. and/or a peak temperature of 251±1° C. (heating rate 10° C./minute).

Polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide has a higher solubility than polymorph 1 and can more easily be purified, and is advantageously isolated in the preparation of 2-(2-methylamino-pyrimidin-4-yl)-1H-indole-5-carboxylic acid [(S)-1-carbamoyl-2-(phenyl-pyrimidin-2-yl-amino)-ethyl]-amide if a further purification is desired, for example by crystallization from, or slurrying with, a suitable solvent system. Polymorph 2 is further characterized by a low hygroscopicity of about 0.4% water uptake at a high relative humidity of 80%. It is furthermore suitable for use in pharmaceutical compositions, or medicaments, in case a higher solubility is advantageous for the desired pharmacological effect of 2-(2-methylamino-pyrimidin-4-yl)-1H-indole-5-carboxylic acid [(S)-1-carbamoyl-2-(phenyl-pyrimidin-2-yl-amino)-ethyl]-amide.

One embodiment of the present invention relates to polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha1}$ (CuK-alpha1) radiation in reflection mode at 2Theta (2θ) angles in degree [°] of 15.2±0.2, 15.9±0.2, 17.3±0.2, 19.2±0.2, 22.2±0.2, 25.3±0.2.

One embodiment of the present invention relates to polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha1}$ (CuK-alpha1) radiation in reflection mode at 2Theta (2θ) angles in degree [°] of 13.9±0.2, 15.2±0.2, 15.9±0.2, 17.3±0.2, 19.2±0.2, 22.2±0.2, 24.5±0.2, 25.3±0.2.

One embodiment of the present invention relates to polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide which has any one or more of the characteristic reflections in an X-ray powder diffractogram using CuK$_{\alpha1}$ radiation in reflection mode which are given above or below herein.

One embodiment of the present invention relates to polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide which has an X-ray powder diffraction pattern substantially as the one shown in FIG. 3 which has been obtained using CuK$_{\alpha 1}$ radiation in reflection mode, wherein the exact relative intensities of the reflections depicted in FIG. 3 are not a prerequisite, but may vary and represent another embodiment of the invention.

Polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide can be obtained from hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide described in the following, and again converted into hydrate 1, and like hydrate 1 is of use in processes for the purification of 2-(2-methylamino-pyrimidin-4-yl)-1H-indole-5-carboxylic acid [(S)-1-carbamoyl-2-(phenyl-pyrimidin-2-yl-amino)-ethyl]-amide, for example by crystallization from, or slurrying with, a suitable solvent system.

One embodiment of the present invention relates to hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha 1}$ (CuK-alpha1) radiation in reflection mode at 2Theta (2θ) angles in degree [°] of 5.3±0.2, 13.5±0.2, 17.9±0.2, 19.5±0.2, 21.5±0.2, 24.9±0.2.

One embodiment of the present invention relates to hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha 1}$ (CuK-alpha1) radiation in reflection mode at 2Theta (2θ) angles in degree [°] of 5.3±0.2, 11.1±0.2, 13.5±0.2, 17.9±0.2, 19.5±0.2, 21.5±0.2, 23.5±0.2, 24.9±0.2, 28.2±0.2.

One embodiment of the present invention relates to hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has any one or more of the characteristic reflections in an X-ray powder diffractogram using CuK$_{\alpha 1}$ radiation in reflection mode which are given above or below herein.

One embodiment of the present invention relates to hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has an X-ray powder diffraction pattern substantially as the one shown in FIG. 4 which has been obtained using CuK$_{\alpha 1}$ radiation in reflection mode, wherein the exact relative intensities of the reflections depicted in FIG. 4 are not a prerequisite, but may vary and represent another embodiment of the invention.

Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide may also be characterized by its crystal parameters which have been determined by single crystal structure analysis. Hydrate 1 crystallizes in the orthorhombic space group P2$_1$2$_1$2$_1$ with the following cell characteristics: Z=4, a=8.18650(10) Å, b=9.97420(10) Å, c=32.8707(2) Å, α=β=γ=90.00° (at 20° C.).

Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide may also be characterized by its behavior in differential scanning calorimetry (DSC), where it gives rise to a broad endothermic peak between room temperature and about 100° C., which can be associated with the loss of water, a sharper endothermic peak at about 170° C., an exothermic peak at about 190° C., and a melting peak at about 253° C. (heating rate 10° C./minute).

In one embodiment of the invention, hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide contains 2±0.3 mol of water, in another embodiment 2±0.1 mol of water, in another embodiment about 2 mol of water, per mol of 2-(2-methylamino-pyrimidin-4-yl)-1H-indole-5-carboxylic acid [(S)-1-carbamoyl-2-(phenyl-pyrimidin-2-yl-amino)-ethyl]-amide, which latter water content was determined by thermogravimetric analysis, for example. Hydrate 1 may thus be termed 2-(2-methylamino-pyrimidin-4-yl)-1H-indole-5-carboxylic acid [(S)-1-carbamoyl-2-(phenyl-pyrimidin-2-yl-amino)-ethyl]-amide dihydrate.

Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide has a higher solubility than polymorph 1 and can more easily be purified, and is advantageously isolated in the preparation of 2-(2-methylamino-pyrimidin-4-yl)-1H-indole-5-carboxylic acid [(S)-1-carbamoyl-2-(phenyl-pyrimidin-2-yl-amino)-ethyl]-amide if a further purification is desired, for example by crystallization from, or slurrying with, a suitable solvent system. Hydrate 1 is further characterized by a low hygroscopicity. It is furthermore suitable for use in pharmaceutical compositions, or medicaments, in case a higher solubility is advantageous for the desired pharmacological effect of 2-(2-methylamino-pyrimidin-4-yl)-1H-indole-5-carboxylic acid [(S)-1-carbamoyl-2-(phenyl-pyrimidin-2-yl-amino)-ethyl]-amide.

One embodiment of the present invention relates to hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha 1}$ (CuK-alpha1) radiation in reflection mode at 2Theta (2θ) angles in degree [°] of 2.9±0.2, 5.3±0.2, 8.3±0.2, 11.5±0.2, 17.1±0.2, 22.8±0.2.

One embodiment of the present invention relates to hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK$_{\alpha 1}$ (CuK-alpha1) radiation in reflection mode at 2Theta (2θ) angles in degree [°] of 2.9±0.2, 5.3±0.2, 6.2±0.2, 8.3±0.2, 9.5±0.2, 11.5±0.2, 14.0±0.2, 17.1±0.2, 18.0±0.2, 22.8±0.2.

One embodiment of the present invention relates to hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has any one or more of the characteristic reflections in an X-ray powder diffractogram using CuK$_{\alpha 1}$ radiation in reflection mode which are given above or below herein.

One embodiment of the present invention relates to hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has an X-ray powder diffraction pattern substantially as the one shown in FIG. 5 which has been obtained using CuK$_{\alpha 1}$ radiation in reflection mode, wherein the exact relative intensities of the reflections depicted in FIG. 5 are not a prerequisite, but may vary and represent another embodiment of the invention.

Hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide may also be characterized by its behavior in differential scanning calorimetry (DSC), where it gives rise to broad endothermic peaks centered around 99° C. and 128° C., a small endothermic peak at 146° C., an exothermic peak at 215° C., and a melting peak around 250° C. (heating rate 10° C./minute).

In one embodiment of the invention, hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide contains 6±0.3 mol of water, in another embodiment 6±0.1 mol of water, in another embodiment about 6 mol of water, per mol of 2-(2-methylamino-pyrimidin-4-yl)-1H-indole-5-carboxylic acid [(S)-1-carbamoyl-2-(phenyl-pyrimidin-2-yl-amino)-ethyl]-amide, which latter water content was determined by thermogravimetric analysis, for example. Hydrate 2 may thus be termed 2-(2-methylamino-pyrimidin-4-yl)-1H-indole-5-carboxylic acid [(S)-1-carbamoyl-2-(phenyl-pyrimidin-2-yl-amino)-ethyl]-amide hexahydrate.

Hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide has a higher solubility than polymorph 1 and can more easily be purified, and is advantageously isolated in the preparation of 2-(2-methylamino-pyrimidin-4-yl)-1H-indole-5-carboxylic acid [(S)-1-carbamoyl-2-(phenyl-pyrimidin-2-yl-amino)-ethyl]-amide if a further purification is desired, for example by crystallization from, or slurrying with, a suitable solvent system. It is furthermore suitable for use in pharmaceutical compositions, or medicaments, in case a higher solubility is advantageous for the desired pharmacological effect of 2-(2-methylamino-pyrimidin-4-yl)-1H-indole-5-carboxylic acid [(S)-1-carbamoyl-2-(phenyl-pyrimidin-2-yl-amino)ethyl]-amide.

One embodiment of the present invention, which is based on the properties of the polymorphs and hydrates such as their solubility specified above, relates to a process for purifying 2-(2-methylamino-pyrimidin-4-yl)-1H-indole-5-carboxylic acid [(S)-1-carbamoyl-2-(phenyl-pyrimidin-2-yl-amino)ethyl]-amide, wherein at least one of polymorph 2, polymorph 3, hydrate 1 and hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide or a mixture of any of them is isolated in the course of the preparation and purification of 2-(2-methylamino-pyrimidin-4-yl)-1H-indole-5-carboxylic acid [(S)-1-carbamoyl-2-(phenyl-pyrimidin-2-yl-amino)-ethyl]-amide.

The present invention further relates to the use of a polymorph or a hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide according to the present invention, selected from polymorphs 1, 2 and 3 and hydrates 1 and 2, or a mixture of polymorphs and hydrates comprising at least one of them, as a pharmaceutical or medicament, which use is based on the pharmacological activity of compound I already described in detail in WO 2004/022553, U.S. Pat. No. 7,285,560, WO 2004/022057 and U.S. Pat. No. 7,462,638, for example. One embodiment of the invention relates to a polymorph selected from polymorphs 1 and 2, or a mixture of polymorphs comprising at least one of polymorphs 1 and 2, for use as a pharmaceutical or medicament. One embodiment of the invention relates to polymorph 1, or a mixture of polymorphs comprising at least polymorph 1, for use as a pharmaceutical or medicament. One embodiment of the invention relates to a hydrate selected from hydrates 1 and 2, or a mixture of polymorphs and/or hydrates comprising at least one of hydrates 1 and 2, for use as pharmaceutical or medicament.

One embodiment of the present invention relates to a pharmaceutical composition which comprises at least one polymorph or hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide according to the present invention, selected from polymorphs 1, 2 and 3 and hydrates 1 and 2, or a mixture of polymorphs and hydrates comprising at least one of them, and one or more pharmaceutically acceptable excipients, i.e. inactive substances such as diluents and other auxiliaries, and which can be employed when using compound I as a pharmaceutical or medicament in human medicine or veterinary medicine. One embodiment of the invention relates to a pharmaceutical composition which comprises at least one of polymorphs 1 and 2, or a mixture of polymorphs comprising at least one of polymorphs 1 and 2, and one or more pharmaceutically acceptable excipients. One embodiment of the invention relates to a pharmaceutical composition which comprises polymorph 1, or a mixture of polymorphs comprising at least polymorph 1, and one or more pharmaceutically acceptable excipients. One embodiment of the invention relates to a pharmaceutical composition which comprises a hydrate selected from hydrates 1 and 2, or a mixture of polymorphs and/or hydrates comprising at least one of hydrates 1 and 2, and one or more pharmaceutically acceptable excipients. If desired, the pharmaceutical compositions according to the invention can also contain one or more other suitable pharmacologically active compounds. The pharmaceuticals, medicaments and pharmaceutical compositions according to the invention can generally be administered by means of oral, inhalative, rectal or transdermal administration or by means of subcutaneous, intraarticular, intraperitoneal or intravenous injection, for example. One embodiment of the invention furthermore relates to a process for preparing a pharmaceutical composition which comprises bringing at least one polymorph or hydrate of 2-(2-methylamino-pyrimidin-4-yl)-1H-indole-5-carboxylic acid [(S)-1-carbamoyl-2-(phenyl-pyrimidin-2-yl-amino)ethyl]-amide according to the present invention, selected from polymorphs 1, 2 and 3 and hydrates 1 and 2, together with one or more pharmaceutically acceptable and physiologically tolerated excipients and, if desired, one or more other suitable pharmacologically active compounds into a suitable form for administration and dosage.

Examples of pharmaceutical compositions are granules, powders, sugar-coated tablets, tablets, (micro)capsules, suppositories, syrups, juices, suspensions, emulsions, drops or injectable solutions, and also preparations with protracted active compound release, in the preparation of which customary auxiliary substances, such as carrier substances, disintegrants, binders, coating agents, swelling agents, glidants or lubricants, flavorings, sweeteners and solubilizers, are used. Frequently employed auxiliary substances which may be mentioned, are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents, such as sterile water and monohydric or polyhydric alcohols, such as glycerol. The pharmaceutical compositions are preferably produced and administered in dosage units, with each unit containing, as the active constituent, a particular dose of at least one polymorph or hydrate according to the invention. In the case of solid dosage units, such as tablets, capsules, sugar-coated tablets or suppositories, this dose can be up to about 1000 mg, preferably from about 50 mg to about 300 mg, and, in the case of injection solutions in ampoule form, up to about 300 mg, preferably from about 1 mg to about 100 mg. The dosage, which is employed when treating a subject, in particular a mammal, specifically a human, with compound I in the form of one or more polymorphs and/or hydrates according to the invention and which is effective for obtaining the desired therapeutic or prophylactic result, varies and is determined by the physician in view of the particulars of the specific case. As is known in the art, the dosage depends on a variety of factors such as, for example, the severity of the condition being treated, general health, the route of administration, body weight, gender, diet, time and route of administration, the desired duration of treatment, rates of absorption and excretion, combination with other drugs, and others.

Because of the pharmacological properties of compound I which are described in WO 2004/022553, U.S. Pat. No. 7,285,560, WO 2004/022057 and U.S. Pat. No. 7,462,638, for example, the polymorphs and hydrates according to the invention can be used for the prophylaxis and therapy of all those diseases whose course involves an increased activity of IκB kinase, for example, chronic diseases of the locomotory apparatus, such as inflammatory, immunologically or metabolism-mediated acute and chronic arthritis, arthropathies, rheumatoid arthritis, or degenerative joint diseases such as osteoarthroses, spondyloses, diabetes Type II, inflammatory bowel disease, loss of cartilage following joint trauma or a relatively long period of joint immobilization following meniscus or patella injuries or ligament ruptures, or diseases of the connective tissue, such as collagenoses and periodontal diseases, myalgias and disturbances of bone metabolism, or diseases which are due to overexpression of tumor necrosis factor alpha (TNFα) or an increased concentration of TNFα, such as cachexia, multiple sclerosis, craniocerebral trauma, Crohn's disease and intestinal ulcers, or diseases such as atherosclerosis, stenoses, ulceration, Alzheimer's diseases, muscle breakdown, cancer diseases (potentiation of treatment with cytotoxic agents), cardiac infarction, gout, sepsis, septic shock, endotoxic shock, viral infections such as flu, hepatitis, HIV infections, AIDS, or diseases caused by adenoviruses or herpes viruses, parasitic infections such as malaria or leprosy, fungal or yeast infections, meningitis, chronic inflammatory lung diseases such as chronic bronchitis or asthma, acute respiratory distress syndrome, acute synovitis, tuberculosis, psoriasis, diabetes, treatment of acute or chronic rejection reactions on the part of the organ recipient against the transplanted organ, chronic graft-versus-host diseases and inflammatory vascular diseases, and they can further be used for the treatment of pain including acute pains and chronic pains, for example pain associated with inflammatory processes or osteoarthritis. Examples of chronic pains which can be treated, are chronic musculoskeletal diseases, such as back pains, pains associated with menstrual bleeding, pains associated with osteoarthritis or rheumatoid arthritis, pains associated with intestinal inflammation, pains associated with cardiac muscle inflammation, pains associated with multiple sclerosis, pains associated with neuritis, pains associated with carcinomas and sarcomas, pains associated with AIDS, pains associated with chemotherapy, amputation pain, trigeminus neuralgia, headaches, such as migraine cephalalgia, or neuropathic pains, such as post-herpes zoster neuralgia. Examples of acute pains which can be treated, are pains following injuries, post-operative pains, pains in association with an acute attack of gout, or acute pains following jawbone surgery interventions.

One embodiment of the present invention relates to a polymorph or a hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide according to the present invention, selected from polymorphs 1, 2 and 3 and hydrates 1 and 2, for use in the treatment of a disease whose course involves an increased activity of IκB kinase, including the use in the treatment of any one or more of the diseases mentioned herein, for example in the treatment of osteoarthritis or pain, as well as the use of such polymorph or hydrate for the manufacture of a medicament for the treatment of a disease whose course involves an increased activity of IκB kinase, including the treatment of any one or more of the diseases mentioned herein, for example the treatment of osteoarthritis or pain, as well as a method for the treatment of a disease whose course involves an increased activity of IκB kinase, including the treatment of any one or more of the diseases mentioned herein, for example the treatment of osteoarthritis or pain, which method comprises administering to a subject in need thereof an effective amount of a polymorph or a hydrate of 2-(2-methylamino-pyrimidin-4-yl)-1H-indole-5-carboxylic acid [(S)-1-carbamoyl-2-(phenyl-pyrimidin-2-yl-amino) ethyl]-amide according to the present invention. One embodiment of the present invention relates to such polymorph of 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of a disease, as well as such use for the manufacture of a medicament, as well as such method for the treatment of a disease, wherein the polymorph is selected from polymorphs 1 and 2, or a mixture of polymorphs comprising at least one of polymorphs 1 and 2. One embodiment of the present invention relates to such polymorph of 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of a disease, as well as such use for the manufacture of a medicament, as well as such method for the treatment of a disease, wherein the polymorph is polymorph 1, or a mixture of polymorphs comprising at least polymorph 1. One embodiment of the present invention relates to such hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of a disease, as well as such use for the manufacture of a medicament, as well as such method for the treatment of a disease, wherein the hydrate is selected from hydrates 1 and 2, or a mixture of polymorphs and/or hydrates comprising at least one of hydrates 1 and 2.

The present invention further relates to processes for the preparation of the polymorphs and hydrates of 2-(2-methylamino-pyrimidin-4-yl)-1H-indole-5-carboxylic acid [(S)-1-carbamoyl-2-(phenyl-pyrimidin-2-yl-amino)ethyl]-amide according to the invention, selected from polymorphs 1, 2 and 3 and hydrates 1 and 2. In general, the polymorphs and hydrates of the invention can be obtained by crystallizing or recrystallizing compound I under suitable conditions for the respective polymorph or hydrate, starting from a solution of compound I or from a suspension of compound I or from solid compound I. A solution or a suspension of compound I for use in the preparation of a desired polymorph or hydrate may directly be obtained at the end of the chemical synthesis of compound I, or it may be obtained by dissolving or suspending previously obtained compound I present in the form of another polymorph or hydrate or a mixture of polymorphs and/or hydrates, which may not be characterized with respect to its crystal properties. Such compound I may be termed "crude compound I". More specifically, the polymorphs and hydrates of the invention may be obtained by providing a solution or suspension of compound I, for example by dissolving or suspending crude compound I in a suitable solvent or solvent mixture, maintaining, heating, cooling and/or concentrating the solution or suspension and/or adding one or more further solvents and/or adding seed crystals of the desired polymorph or hydrate, with or without agitation such as stirring, to form a precipitate of crystals of a desired polymorph or hydrate or to allow the formation of the desired polymorph or hydrate, and isolating the desired polymorph or hydrate. Seeding with a small amount of the desired polymorph or hydrate is a preferred procedure for promoting crystallization of the desired form. The preparation of the polymorphs and hydrates of compound I can be performed with conventional equipment and according to standard procedures. For example, concentrating a solution or suspension may be done by distilling off solvent partially or totally at atmospheric pressure or at reduced pressure. Isolating a polymorph or hydrate may be done by any conventional technique such as filtration or vacuum filtration or centrifugation. Isolating may also include washing of the initially separated solid and/or drying, for example at room temperature and atmospheric pressure or elevated temperature and/or reduced pressure.

Compound I, i.e. 2-(2-methylamino-pyrimidin-4-yl)-1H-indole-5-carboxylic acid [(S)-1-carbamoyl-2-(phenyl-pyrimidin-2-yl-amino)-ethyl]-amide, can be prepared as described in WO 2004/022553 and U.S. Pat. No. 7,285,560, for example, and detailed further below herein. In brief, for the synthesis of compound I 2-[bis-(tert-butoxycarbonyl)]amino-3-(phenyl-pyrimidin-2-yl-amino)propionic acid methyl ester, which is available from 2-[di-(tert-butoxycarbonyl)amino]acrylic acid methyl ester and 2-anilino-pyrimidine as described in WO 2004/022553 and U.S. Pat. No. 7,285,560, for example, is deprotected by treatment with an acid such as hydrochloric acid, and the obtained racemic 2-amino-3-(phenyl-pyrimidin-2-yl-amino)propionic acid methyl ester separated into the enantiomers by preparative high pressure liquid chromatography on a chiral phase under standard conditions. The obtained (S)-2-amino-3-(phenyl-pyrimidin-2-yl-amino)propionic acid methyl ester is reacted with 2-(2-methylaminopyrimidin-4-yl)-1H-indole-5-carboxylic acid, whose synthesis is described in WO 2004/022553 and U.S. Pat. No. 7,285,560, for example, by means of a coupling agent such as N,N,N',N'-tetramethyl-O-(7-azabenzotriazol-1-yl)-uronium hexafluorophosphate (HATU) in the presence of a base like diisopropylethylamine to give (S)-2-{[2-(2-methylaminopyrimidin-4-yl)-1H-indole-5-carbonyl]amino}-3-(phenyl-pyrimidin-2-yl-amino)propionic acid methyl ester, which in the last step is reacted with ammonia to give 2-(2-methylamino-pyrimidin-4-yl)-1H-indole-5-carboxylic acid [(S)-1-carbamoyl-2-(phenyl-pyrimidin-2-yl-amino)-ethyl]-amide, which may also be named as (S)-2-{[2-(2-methylaminopyrimidin-4-yl)-1H-indole-5-carbonyl]amino}-3-(phenyl-pyrimidin-2-yl-amino)propionamide, for example.

If the last step in the aforesaid synthesis of 2-(2-methylamino-pyrimidin-4-yl)-1H-indole-5-carboxylic acid [(S)-1-carbamoyl-2-(phenyl-pyrimidin-2-yl-amino)-ethyl]-amide is performed by reacting (S)-2-{[2-(2-methylaminopyrimidin-4-yl)-1H-indole-5-carbonyl]amino}-3-(phenyl-pyrimidin-2-yl-amino)propionic acid methyl ester with a less than saturated solution of ammonia in methanol, such as a 7N solution of ammonia in methanol, at room temperature, i.e. at about 20 to 25° C., for a longer period of time such as three days, and the precipitated solid is directly isolated by filtration, polymorph 1 of 2-(2-methylamino-pyrimidin-4-yl)-1H-indole-5-carboxylic acid [(S)-1-carbamoyl-2-(phenyl-pyrimidin-2-yl-amino)ethyl]-amide is obtained. One embodiment of the present invention thus relates to a process for preparing polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises reacting (S)-2-{[2-(2-methylaminopyrimidin-4-yl)-1H-indole-5-carbonyl]amino}-3-(phenyl-pyrimidin-2-yl-amino)propionic acid methyl ester with a solution of ammonia in methanol, for example a 7N solution, at room temperature for a sufficient period of time, for example about three days, and isolating the precipitated solid.

Instead of by reacting (S)-2-amino-3-(phenyl-pyrimidin-2-yl-amino)propionic acid methyl ester with 2-(2-methylaminopyrimidin-4-yl)-1H-indole-5-carboxylic acid and subsequently converting the ester group into the amide group by reaction with ammonia, 2-(2-methylamino-pyrimidin-4-yl)-1H-indole-5-carboxylic acid [(S)-1-carbamoyl-2-(phenyl-pyrimidin-2-yl-amino)-ethyl]-amide can also be prepared according to other synthetic procedures, for example by reacting 2-(2-methylamino-pyrimidin-4-yl)-1H-indole-5-carboxylic acid, or a salt thereof which renders the addition of a base unnecessary, such as the sodium salt of 2-(2-methylamino-pyrimidin-4-yl)-1H-indole-5-carboxylic acid whose synthesis is described in WO 2006/128585 and US 2008/0214813, for example, with (S)-2-amino-3-(phenyl-pyrimidin-2-yl-amino)-propionamide, whose synthesis is described in PCT/EP2011/063504, for example, in the presence of a coupling agent, such as 1-(3-dimethylaminopropyl)-3-ethylcarbodiimide hydrochloride, optionally in the presence of a base, as is detailed further below herein.

If the aforesaid synthesis of 2-(2-methylamino-pyrimidin-4-yl)-1H-indole-5-carboxylic acid [(S)-1-carbamoyl-2-(phenyl-pyrimidin-2-yl-amino)ethyl]-amide from (S)-2-amino-3-(phenyl-pyrimidin-2-yl-amino)-propionamide is performed in a mixture of tetrahydrofuran and N-methylpyrrolidin-2-one as solvent at room temperature, i.e. at about 20 to 25° C., and for work-up the reaction mixture is diluted with water and the precipitated solid is directly isolated by filtration, hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide is obtained. One embodiment of the present invention thus relates to a process for preparing hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises reacting 2-(2-methylamino-pyrimidin-4-yl)-1H-indole-5-carboxylic acid or a salt thereof with (S)-2-amino-3-(phenyl-pyrimidin-2-yl-amino)-propionamide in the presence of a coupling agent, for example 1-(3-dimethylaminopropyl)-3-ethylcarbodiimide hydrochloride, optionally in the presence of a base, in a mixture of tetrahydrofuran and N-methylpyrrolidin-2-one at room temperature, diluting the reaction mixture with water and isolating the precipitated solid.

Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide can be converted in one or more steps into other crystalline forms of 2-(2-methylamino-pyrimidin-4-yl)-1H-indole-5-carboxylic acid [(S)-1-carbamoyl-2-(phenyl-pyrimidin-2-yl-amino)ethyl]-amide, such as polymorphs 1, 2 and 3 and hydrate 2.

For example, by heating hydrate 1 in a suitable solvent, optionally seeding with the desired crystalline form and cooling the mixture, polymorphs 1 and 2 can be obtained. For the conversion into polymorph 1, for example, hydrate 1 can be heated in acetone to a temperature of about 35° C. to about reflux temperature, for example to about 40° C., the mixture seeded with a small amount of polymorph 1, kept at about 40° C. for some time, for example about 5 to about 10 hours, such as about 6 hours, cooled to room temperature and the solid isolated. One embodiment of the present invention thus relates to a process for preparing polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises heating hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide in acetone in the presence of seed crystals of polymorph 1, for example to about 40° C., for a time period of about 5 to about 10 hours, for example for about 6 hours, cooling the mixture to room temperature and isolating the precipitated solid.

For the conversion into polymorph 2, hydrate 1 can be heated in a mixture of diisopropyl ether and methanol to a temperature of about 60 to about 70° C., for example to about reflux temperature or to about 68° C., kept at this temperature for some time, for example about 18 to about 30 hours, such as about 24 hours, cooled to room temperature and the solid isolated. One embodiment of the present invention thus relates to a process for preparing polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises heating hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide in a mixture of diisopropyl ether and methanol, for example to about 60 to about 70° C., for a time period of about 18 to about 30 hours, for example for about 24 hours, cooling the mixture to about 20 to 25° C. and isolating the precipitated solid. In one embodiment of this latter process for preparing polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, the mixture of diisopropyl ether and methanol contains from about 3 to about 10%, in another embodiment from about 4 to about 8%, in another embodiment about 6%, of methanol by weight.

For the conversion into polymorph 3, hydrate 1 can be dried in substance at elevated temperature and reduced pressure, for example at about 50 to about 70° C., such as at about 60° C., and about 20 to about 50 mbar, for example about 30 mbar, for example in a standard drying cabinet, for a time period sufficient for the transformation of the dihydrate into the anhydrous form of polymorph 3, for example for about 18 to about 30 hours, such as about 24 hours. One embodiment of the present invention thus relates to a process for preparing polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises drying hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide at a temperature of about 50 to about 70° C. and a pressure from about 20 to about 50 mbar for a time period of about 18 to about 30 hours.

Polymorph 3 can be re-converted into hydrate 1 by exposing it to an atmosphere which contains water vapor, for example leaving it uncovered in the air at room temperature, i.e. at about 20 to 25° C., and atmospheric pressure for a time period sufficient for the transformation of the anhydrous form into the dihydrate, for example for about 15 to about 25 hours, such as about 17 hours. One embodiment of the present invention thus relates to a process for preparing hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises allowing polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide to take up water from the surrounding atmosphere at a temperature of about 20 to about 25° C. for a time period of about 15 to about 25 hours.

Polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, which can be obtained from hydrate 1 as outlined above, for example, can be converted by heating in a suitable solvent, optionally seeding with the desired crystalline form, and optionally cooling the mixture, into polymorph 1 and hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide.

For example, for the conversion into polymorph 1, polymorph 2 can be heated in a mixture of acetone and water to a temperature of about 50 to about 60° C., for example to about reflux temperature or to about 60° C., kept at this temperature for some time, for example about 1 to about 5 hours, such as about 2 to about 3 hours, cooled to room temperature, and the solid isolated. One embodiment of the present invention thus relates to a process for preparing polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises heating polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide in a mixture of acetone and water, for example to about 50 to about 60° C., for a time period of about 1 to about 5 hours, for example for about 2 to about 3 hours, cooling the mixture to about 20 to 25° C. and isolating the precipitated solid. In one embodiment of this latter process for preparing polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, the mixture of acetone and water contains from about 3 to about 6 parts of acetone per part of water, in another embodiment from about 3 to about 5 parts of acetone per part of water, in another embodiment about 4 parts of acetone per part of water, in each case parts by volume.

For the conversion into hydrate 2, polymorph 2 can be heated in a mixture of acetone and water to a temperature of about 30 to about 40° C., for example to about 40° C., kept at this temperature for some time, for example about 2 to about 10 hours, such as about 4 hours, cooled to room temperature and the solid isolated. One embodiment of the present invention thus relates to a process for preparing hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, which comprises heating polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide in a mixture of acetone and water, for example to about 40° C., for a time period of about 2 to about 10 hours, for example for about 4 hours, cooling the mixture to about 20 to 25° C., and isolating the precipitated solid. In one embodiment of this process for preparing hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, the mixture of acetone and water contains from about 1 to about 3 parts of acetone per part of water, in another embodiment about 2 parts of acetone per part of water, in each case parts by volume.

DESCRIPTION OF THE FIGURES

FIG. 5. X-ray powder diffraction pattern of hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, measured in reflection mode with CuK$_{\alpha 1}$ radiation at room temperature; x-axis: diffraction angle 2Theta (degree); y-axis: intensity (counts in arbitrary unit).

Figure 1:
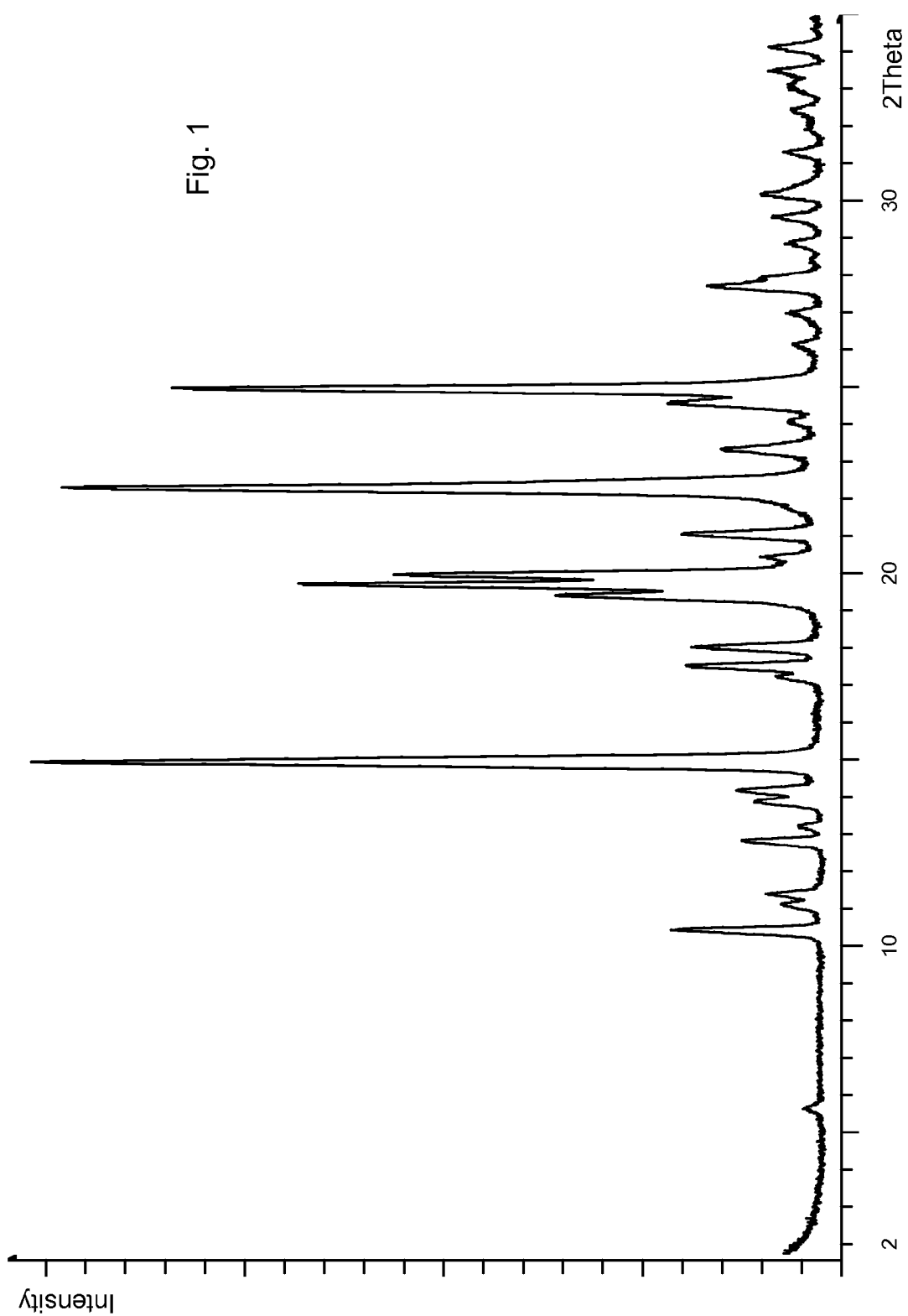
FIG. 1. X-ray powder diffraction pattern of polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, measured in reflection mode with $CuK_{\alpha 1}$ radiation at room temperature; x-axis: diffraction angle 2Theta (degree); y-axis: intensity (counts in arbitrary unit).

In the following, the formation and characterization of the polymorphs and hydrates of the present invention is described in detail by way of example.

EXAMPLES

Example 1

Formation of polymorph 1 of 2-(2-methylamino-pyrimidin-4-yl)-1H-indole-5-carboxylic acid [(S)-1-carbamoyl-2-(phenyl-pyrimidin-2-yl-amino)ethyl]-amide (a) 2-Amino-3-(phenyl-pyrimidin-2-yl-amino)propionic acid methyl ester 470 ml of 5N hydrochloric acid were added dropwise to a solution of 100 g (212 mmol) of 2-[bis-(tert-butoxycarbonyl)]amino-3-(phenyl-pyrimidin-2-yl-amino)propionic acid methyl ester in 1000 ml of isopropyl acetate at 15° C., and the mixture was stirred for 2 h. Then the phases were separated and the pH of the aqueous phase was adjusted to 8.5 by addition of an aqueous solution of ammonia under cooling in an ice bath. The aqueous phase was extracted with ethyl acetate, and the extract washed with a saturated solution of sodium chloride, dried over sodium sulfate and evaporated in vacuo to give 52.8 g (92%) of 2-amino-3-(phenyl-pyrimidin-2-yl-amino)propionic acid methyl ester as a yellow oil.

MS (ESI): m/z=273 (M$^+$+1, 100%); $^1$H-NMR (500 MHz, DMSO-d$_6$): δ=8.31 (d (doublet), J=4.8 Hz, 2 H), 7.40 (m (multiplet), 2 H), 7.33-7.20 (m, 3 H), 6.70 (t (triplet), J=4.8 Hz, 1 H), 4.18 (dd (double doublet), J=9.6 and 14.4 Hz, 1 H), 4.05 (dd, J=9.5 and 14.3 Hz, 1 H), 3.65 (t, J=9.6 Hz, 1 H), 3.43 (s (singlet), 3 H), 1.88 ppm (bs (broad singlet), 2 H); HPLC (column: Chiralcel OJ-H, 250×4.6 mm; eluent: n-heptane+0.1% diethylamine:ethanol+0.1% diethylamine (85:15); flow rate: 1 ml/min; detection wavelength: 285 nm): retention time=14.6 min (S enantiomer) and 16.4 min (R enantiomer).

(b) (R)-2-Amino-3-(phenyl-pyrimidin-2-yl-amino)propionic acid methyl ester and (S)-2-amino-3-(phenyl-pyrimidin-2-yl-amino)propionic acid methyl ester 10 g of 2-amino-3-(phenyl-pyrimidin-2-yl-amino)propionic acid methyl ester were separated into the enantiomers by preparative HPLC on a chiral phase (column: Chiralpak AS-H, 250×30 mm; eluent: n-heptane:ethanol (5:1); flow rate: 30 ml/min; detection wavelength: 257 nm; retention time of the S enantiomer: 12.5 min, retention time of the R enantiomer: 18.1 min). 2.6 g (52%) of (R)-2-amino-3-(phenyl-pyrimidin-2-yl-amino)propionic acid methyl ester and 2.6 g (52%) of (S)-2-amino-3-(phenyl-pyrimidin-2-yl-amino)propionic acid methyl ester were obtained.

(c) (S)-2-{[2-(2-Methylaminopyrimidin-4-yl)-1H-indole-5-carbonyl]amino}-3-(phenyl-pyrimidin-2-yl-amino)propionic acid methyl ester 4.01 g (10.6 mmol) of N,N,N',N'-tetramethyl-O-(7-azabenzotriazol-1-yl)-uronium hexafluorophosphate and 6.82 g (52.8 mmol) of diisopropylethylamine were added to a solution of 2.36 g (8.80 mmol) of 2-(2-methylaminopyrimidin-4-yl)-1H-indole-5-carboxylic acid in 80 ml of dimethylformamide under cooling with an ice bath, and the mixture was stirred at 0° C. for 1.5 h. Then a solution of 2.40 g (8.80 mmol) of (S)-2-amino-3-(phenyl-pyrimidin-2-yl-amino)propionic acid methyl ester (98.9% ee (enantiomeric excess)) in 22 ml of dimethylformamide was added. The mixture was stirred for 2 h, and then an aqueous solution of sodium hydrogencarbonate and isopropyl acetate were added. The organic phase was separated, washed with a saturated solution of sodium chloride and concentrated in vacuo. The solid that precipitated was filtered off with suction, dried in vacuo and purified by column chromatography (silica gel, dichloromethane:methanol (25:1)). 2.35 g (50%) of (S)-2-{[2-(2-methylaminopyrimidin-4-yl)-1H-indole-5-carbonyl]amino}-3-(phenyl-pyrimidin-2-yl-amino)propionic acid methyl ester were obtained as a yellowish solid.

MS (ESI): m/z=522 (M$^+$, 100%); $^1$H-NMR (600 MHz, DMSO-d$_6$): δ=11.7 (s, 1 H), 8.78 (m, 1 H), 8.40 (d, J=4.8 Hz, 2 H), 8.32 (bs, 1 H), 8.05 (s, 1 H), 7.60 (d, J=8.5 Hz, 1 H), 7.52 (d, J=8.5 Hz, 1 H), 7.40-7.14 (m, 7 H), 7.00 (bs, 1 H), 6.78 (t, J=4.8 Hz, 1 H), 4.90 (m, 1 H), 4.68 (dd, J=6.9 and 9.4 Hz, 1 H), 4.29 (dd, J=7.1 and 9.3 Hz, 1 H), 3.54 (s, 3 H), 2.95 ppm (bs, 3 H); HPLC (column: Chiralcel OD-H, 250×4.6 mm; eluent: n-heptane:ethanol (60:40), flow rate: 1 ml/min, detection wavelength: 254 nm): retention time=10.1 min (R enantiomer) and 15.0 min (S enantiomer); ee of the S enantiomer=94.7%.

(d) 2-(2-Methylamino-pyrimidin-4-yl)-1H-indole-5-carboxylic acid [(S)-1-carbamoyl-2-(phenyl-pyrimidin-2-yl-amino)-ethyl]-amide A solution of 2.20 g (4.21 mmol) of (S)-2-{[2-(2-methylaminopyrimidin-4-yl)-1H-indole-5-carbonyl]amino}-3-(phenyl-pyrimidin-2-yl-amino)propionic acid methyl ester (94.7% ee) in 220 ml of a 7N solution of ammonia in methanol was stirred at room temperature for three days. The solid that precipitated was filtered off with suction and dried in vacuo. 1.75 g (82%) of polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, identified by its X-ray powder diffractogram, were obtained as a colorless solid.

MS (ESI): m/z=507 (M$^+$, 100%); $^1$H-NMR (400 MHz, DMSO-d$_6$): δ=11.7 (s, 1 H), 8.40 (d, J=4.8 Hz, 2 H), 8.34 (m, 2 H), 7.92 (s, 1 H), 7.55 (d, J=8.5 Hz, 1 H), 7.50 (d, J=8.5 Hz, 1 H), 7.43-7.10 (m, 9 H), 7.00 (bs, 1 H), 6.77 (t, J=4.8 Hz, 1 H), 4.80 (m, 1 H), 4.53 (dd, J=10.0 and 14.4 Hz, 1 H), 4.25 (dd, J=4.2 and 14.3 Hz, 1 H), 2.96 ppm (bs, 3 H); HPLC (column: Chiralcel OD-H, 250×4.6 mm; eluent: n-heptane:ethanol (50:50), flow rate: 1 ml/min, detection wavelength:

238 nm): retention time=10.2 min (R enantiomer) and 14.5 min (S enantiomer); ee of the S enantiomer=99.2%.

Example 2

Formation of hydrate 1 of 2-(2-methylamino-pyrimidin-4-yl)-1H-indole-5-carboxylic acid [(S)-1-carbamoyl-2-(phenyl-pyrimidin-2-yl-amino)ethyl]-amide 40 ml of tetrahydrofuran and 10 ml of N-methylpyrrolidin-2-one were added to 5 g of (S)-2-amino-3-(phenyl-pyrimidin-2-yl-amino)-propionamide, 5.65 g of 2-(2-methylamino-pyrimidin-4-yl)-1H-indole-5-carboxylic acid sodium salt and 7 g of 1-(3-dimethylaminopropyl)-3-ethylcarbodiimide hydrochloride at room temperature. The mixture was stirred at room temperature for 2 h. Then 500 ml of water were slowly added. From the resulting solution, a solid precipitated which was filtered off with suction and washed with 50 ml of water and dried at room temperature until constant weight was achieved, to give 7.46 g of hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide identified by its X-ray powder diffractogram.

Example 3

Formation of hydrate 2 of 2-(2-methylamino-pyrimidin-4-yl)-1H-indole-5-carboxylic acid [(S)-1-carbamoyl-2-(phenyl-pyrimidin-2-yl-amino)ethyl]-amide 1.52 g of polymorph 2 of 2-(2-methylamino-pyrimidin-4-yl)-1H-indole-5-carboxylic acid [(S)-1-carbamoyl-2-(phenyl-pyrimidin-2-yl-amino)ethyl]-amide in 20 ml of a mixture of acetone and water (2:1, by volume) was heated to 40° C. and the suspension stirred at this temperature for 4 h. A sample of about 1 ml of the suspension was taken, the solid filtered off with suction and dried at room temperature until constant weight was achieved, to give hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide identified by its X-ray powder diffractogram.

Example 4

Formation of polymorph 3 of 2-(2-methylamino-pyrimidin-4-yl)-1H-indole-5-carboxylic acid [(S)-1-carbamoyl-2-(phenyl-pyrimidin-2-yl-amino)ethyl]-amide Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide was placed in a vacuum drying cabinet and dried at a pressure of 30 mbar and a temperature of 60° C. for 24 h to give polymorph 3 of 2-(2-methylamino-pyrimidin-4-yl)-1H-indole-5-carboxylic acid [(S)-1-carbamoyl-2-(phenyl-pyrimidin-2-yl-amino)ethyl]-amide identified by its X-ray powder diffractogram. The water content of the product determined by Karl Fischer titration was 0.09%.

Example 5

Formation of polymorph 2 of 2-(2-methylamino-pyrimidin-4-yl)-1H-indole-5-carboxylic acid [(S)-1-carbamoyl-2-(phenyl-pyrimidin-2-yl-amino)ethyl]-amide 16.7 g of diisopropyl ether and 1.0 g of methanol were added to 0.5 g of hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide in a reaction vessel, and the suspension placed in a shaking device (Heidolph Synthesis 1; adjusted to 500 rpm) and heated to reflux at an internal temperature of 68° C. The mixture was kept at this temperature for 24 h, and allowed to cool to room temperature. The solid was filtered off with suction and air-dried at room temperature for 8 h to give polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide identified by its X-ray powder diffractogram.

Example 6

Formation of hydrate 1 of 2-(2-methylamino-pyrimidin-4-yl)-1H-indole-5-carboxylic acid [(S)-1-carbamoyl-2-(phenyl-pyrimidin-2-yl-amino)ethyl]-amide Polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide was kept in the air at room temperature for 17 h to give hydrate 1 of 2-(2-methylamino-pyrimidin-4-yl)-1H-indole-5-carboxylic acid [(S)-1-carbamoyl-2-(phenyl-pyrimidin-2-yl-amino)ethyl]-amide identified by its X-ray powder diffractogram.

Example 7

Formation of polymorph 1 of 2-(2-methylamino-pyrimidin-4-yl)-1H-indole-5-carboxylic acid [(S)-1-carbamoyl-2-(phenyl-pyrimidin-2-yl-amino)ethyl]-amide 1.0 g of polymorph 2 of 2-(2-methylamino-pyrimidin-4-yl)-1H-indole-5-carboxylic acid [(S)-1-carbamoyl-2-(phenyl-pyrimidin-2-yl-amino)ethyl]-amide and 15 ml of a mixture of acetone and water (4:1, by volume) were heated with stirring to an internal temperature of 60° C. The mixture was kept at this temperature for 2.5 h and then cooled to 24° C. within 1 h The solid was filtered off with suction, washed twice with 5 ml each of water and dried in vacuo at a pressure of 50 mbar and a temperature of 60° C. for 19 h, to give 0.89 g of polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide identified by its X-ray powder diffractogram.

Example 8

Formation of polymorph 1 of 2-(2-methylamino-pyrimidin-4-yl)-1H-indole-5-carboxylic acid [(S)-1-carbamoyl-2-(phenyl-pyrimidin-2-yl-amino)ethyl]-amide 0.6 g of hydrate 1 of 2-(2-methylamino-pyrimidin-4-yl)-1H-indole-5-carboxylic acid [(S)-1-carbamoyl-2-(phenyl-pyrimidin-2-yl-amino)ethyl]-amide and 15 ml of acetone in a reaction vessel were placed in a shaking device (Heidolph Synthesis 1; adjusted to 500 rpm). The mixture was seeded with a small amount of polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, heated to an internal temperature of 40° C., and kept at this temperature for 6 h. A sample of about 1 ml of the suspension was taken, the solid filtered off and dried at room temperature until constant weight was achieved to give polymorph 1 of 2-(2- methylamino-pyrimidin-4-yl)-1H-indole-5-carboxylic acid [(S)-1-carbamoyl-2-(phenyl-pyrimidin-2-yl-amino)ethyl]-amide identified by its X-ray powder diffractogram.

Analytical Methods

X-Ray Powder Diffraction (XRPD)

X-ray powder diffraction measurements were performed with a Bruker AXS D8 Advance diffractometer in reflection mode using $CuK_{\alpha1}$ (CuK-alpha1) radiation. Unless stated otherwise, X-ray powder diffraction was performed at room temperature. Samples were investigated in a flat preparation. The measured data were visualized and evaluated with the Software EVA 12.0.

Figure 2:
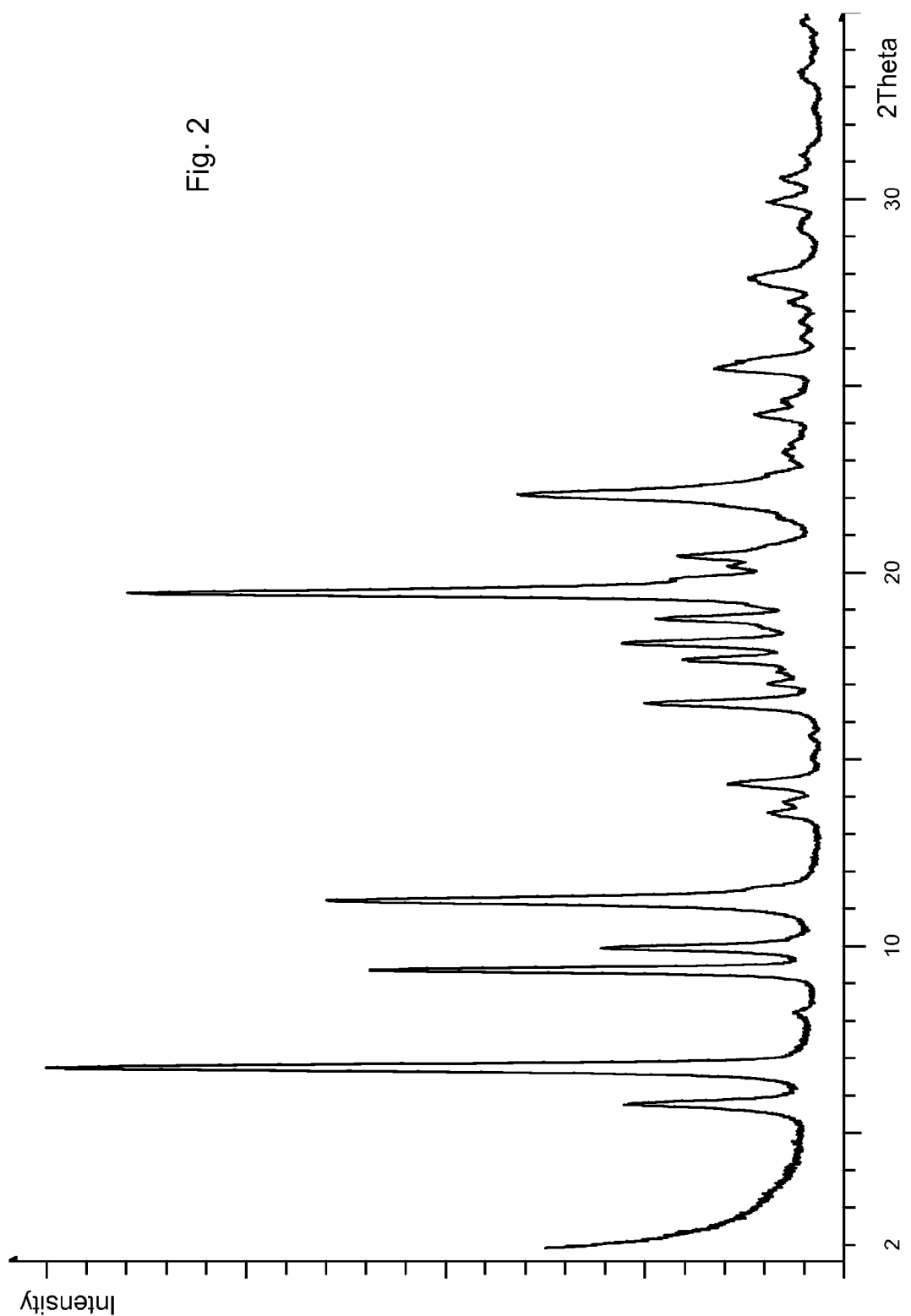
FIG. 2. X-ray powder diffraction pattern of polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide, measured in reflection mode with $CuK_{\alpha 1}$ radiation at room temperature; x-axis: diffraction angle 2Theta (degree); y-axis: intensity (counts in arbitrary unit).
Figure 3:
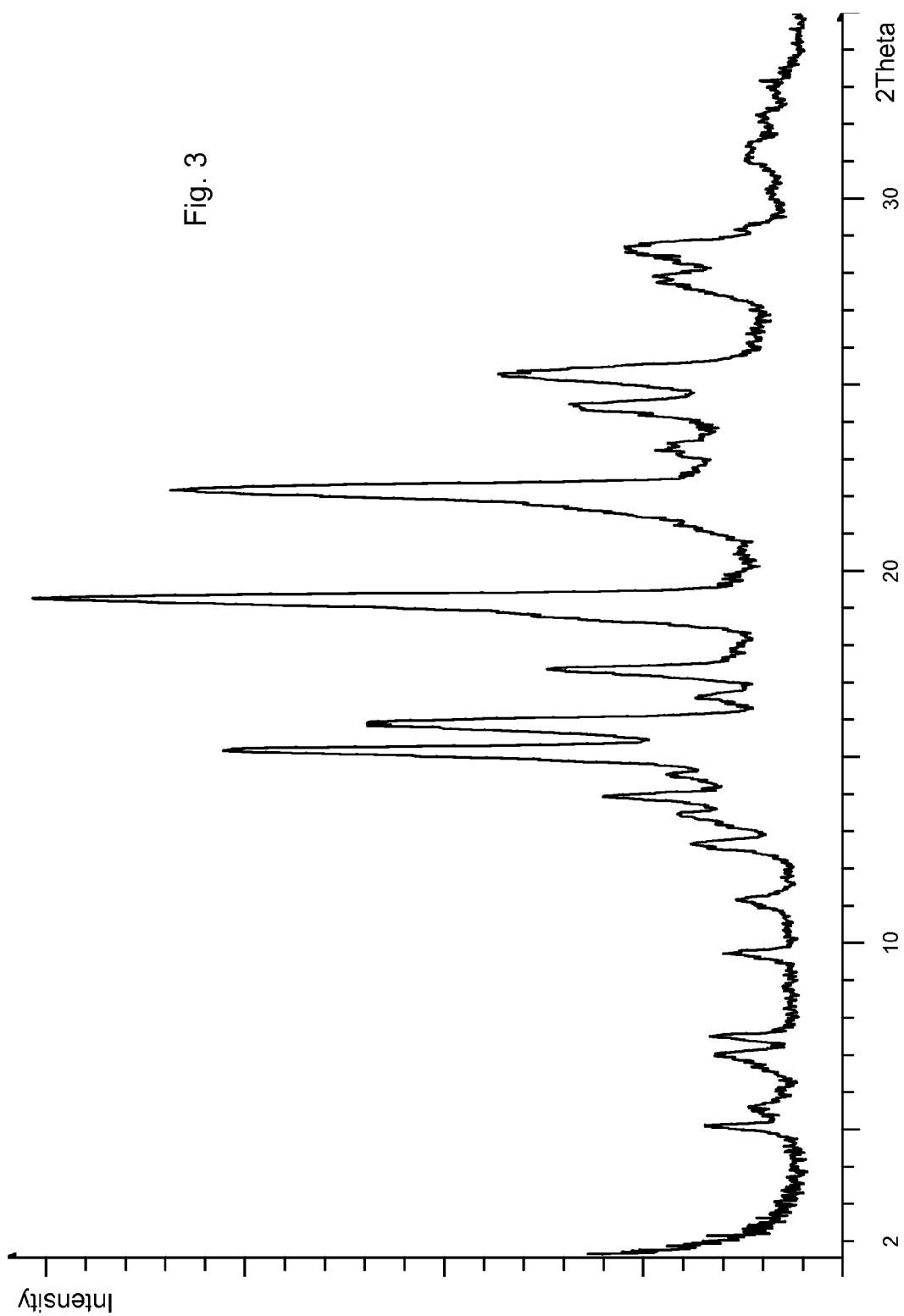
FIG. 3. X-ray powder diffraction pattern of polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide, measured in reflection mode with CuK$_{\alpha 1}$ radiation at room temperature; x-axis: diffraction angle 2Theta (degree); y-axis: intensity (counts in arbitrary unit).
Figure 4:
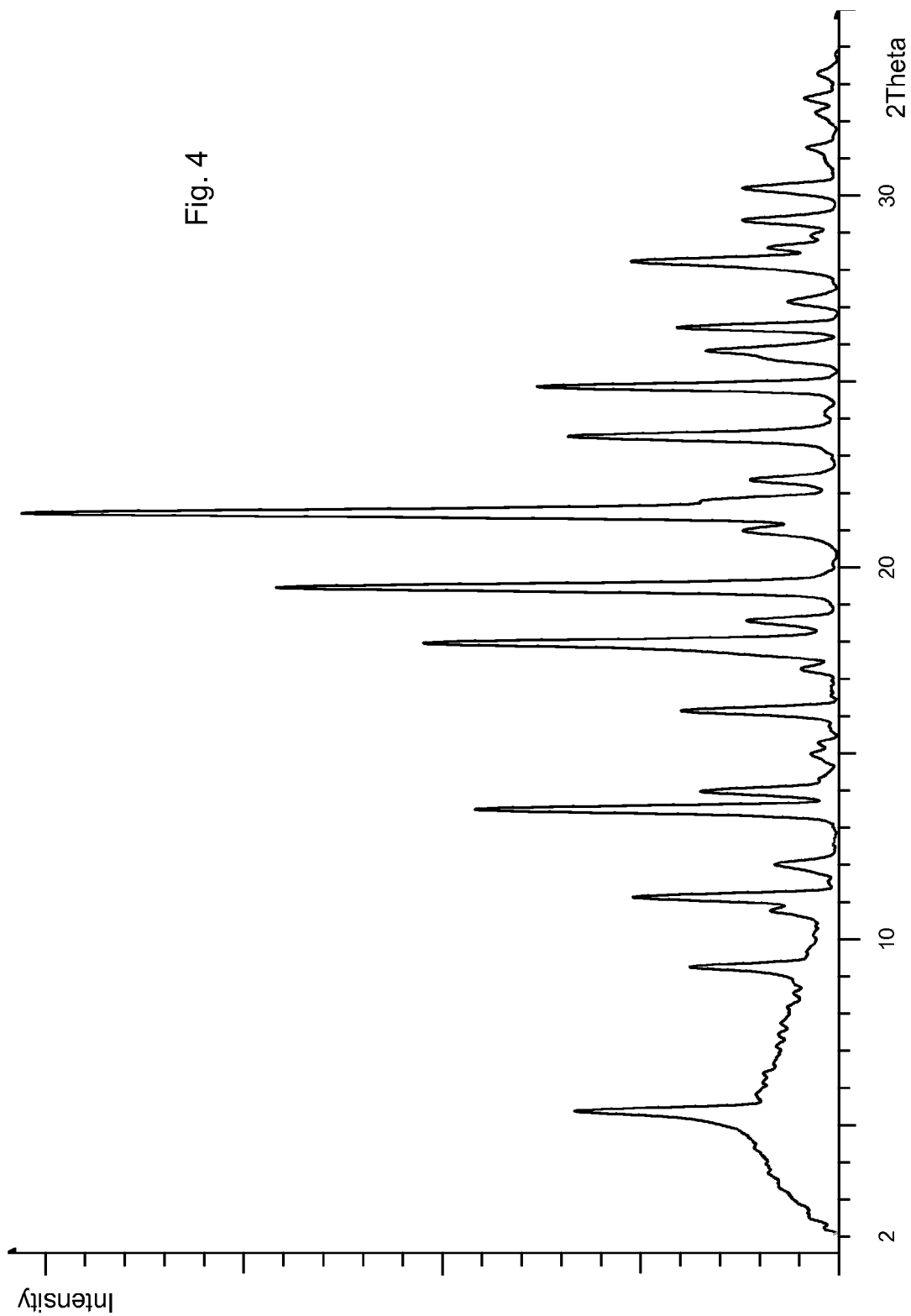
FIG. 4. X-ray powder diffraction pattern of hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide, measured in reflection mode with CuK$_{\alpha 1}$ radiation at room temperature; x-axis: diffraction angle 2Theta (degree); y-axis: intensity (counts in arbitrary unit).

X-ray powder diffractograms of polymorphs 1, 2 and 3 and hydrates 1 and 2 of compound I are displayed in FIGS. 1 to 5. The data of observed X-ray reflections are given below in the following form: angle 2Theta (2θ) in ° (degree), followed in brackets by the relative intensity in % of the intensity of the strongest reflection whose intensity was set to 100% (the intensities are measured in counts in arbitrary unit). The given data are rounded to multiples of 0.1° and 1%, respectively. As indicated above, the given angles 2Theta may be understood as lying within an margin of ±0.2°, and the relative intensities may vary to a greater extent depending on the sample and measurement conditions, and the given exact values of the relative intensities are not to be regarded as a prerequisite for the presence of a crystalline form. For a classification, reflections with a relative intensity of more than 60% of the strongest reflection, for example, may be termed as strong reflections, and reflections with a relative intensity between 30% and 60% of the strongest reflection, for example, may be termed as medium strong reflections, and such medium strong reflections and/or strong reflections used to characterize the polymorphs and hydrates of compound I.

XRPD Reflections of Polymorph 1 (2Theta [°], Relative Intensity [%])

5.6° (5%), 10.4° (21%), 11.1° (8%), 11.4° (10%), 12.8° (13%), 13.2° (6%), 13.9° (11%), 14.2° (13%), 14.9° (100%), 17.2° (8%), 17.5° (19%), 18.0° (19%), 19.4° (35%), 19.7° (67%), 20.0° (55%), 20.4° (10%), 21.0° (20%), 22.3° (96%), 23.3° (15%), 24.1° (7%), 24.6° (21%), 25.0° (82%), 26.1° (6%), 27.0° (6%), 27.7° (16%), 28.9° (7%), 29.6° (9%), 30.2° (10%), 31.3° (7%), 31.9° (4%), 32.4° (6%), 33.1° (6%)

XRPD Reflections of Polymorph 2 (2Theta [°], Relative Intensity [%])

5.8° (27%), 6.7° (100%), 8.2° (7%), 9.3° (60%), 9.9° (31%), 11.2° (65%), 13.5° (9%), 13.8° (8%), 14.3° (15%), 16.5° (25%), 17.0° (10%), 17.7° (21%), 18.1° (28%), 18.8° (24%), 19.4° (89%), 20.2° (15%), 20.4° (21%), 22.1° (41%), 24.2° (11%), 24.6° (8%), 25.5° (16%), 27.9° (12%), 30.0° (10%), 30.6° (8%)

XRPD Reflections of Polymorph 3 (2Theta [°], Relative Intensity [%])

5.1° (17%), 5.6° (12%), 7.0° (16%), 7.5° (16%), 9.7° (14%), 11.2° (13%), 12.7° (19%), 13.4° (20%), 13.9° (30%), 15.2° (76%), 15.9° (59%), 16.6° (18%), 17.3° (36%), 19.2° (100%), 22.2° (83%), 23.2° (23%), 24.5° (33%), 25.3° (42%), 27.9° (23%), 28.7° (27%)

XRPD Reflections of Hydrate 1 (2Theta [°], Relative Intensity [%])

5.3° (33%), 9.2° (19%), 10.7° (9%), 11.1° (25%), 12.0° (8%), 13.5° (44%), 14.0° (17%), 16.1° (20%), 17.2° (5%), 17.9° (51%), 18.5° (12%), 19.5° (69%), 21.0° (12%), 21.5° (100%), 22.4° (11%), 23.5° (33%), 24.9° (37%), 25.8° (16%), 26.5° (20%), 27.2° (7%), 28.2° (26%), 28.6° (9%), 29.4° (12%), 30.2° (12%), 31.3° (4%), 32.3° (3%), 32.7° (4%), 33.3° (3%)

XRPD Reflections of Hydrate 2 (2Theta [°], Relative Intensity [%])

2.9° (100%), 5.3° (29%), 6.2° (9%), 8.3° (33%), 9.5° (13%), 11.0° (3%), 11.5° (28%), 12.8° (4%), 14.0° (11%), 14.7° (4%), 16.1° (3%), 16.8° (4%), 17.1° (14%), 18.0° (11%), 18.8° (4%), 19.7° (3%), 20.3° (6%), 21.3° (11%), 21.9° (6%), 22.8° (14%), 23.5° (7%), 24.7° (5%), 25.5° (4%), 26.1° (9%), 27.3° (5%), 28.6° (5%), 29.6° (4%), 30.1° (3%), 31.4° (3%), 31.8° (5%), 34.9° (4%)

Crystal Structure Determination

The crystal structure of hydrate 1 of compound I was determined by X-ray single crystal structure analysis with a crystal obtained by crystallization from a mixture of acetone and water (4:1) and sealed in a Lindemann-glass capillary. Single crystal X-ray diffraction data were collected on a Bruker/AXS three circle diffractometer, equipped with a SMART APEX area detector, a low temperature device (model LT2) and a copper micro focus generator (IμS), operated at 45 kV/650 mA, and focusing beam Montel multilayer optic with an image focus spot diameter of ~250 μm. Data processing was done with the program SAINT+ Release 6.45. Hydrate 1 of compound I crystallizes in the orthorhombic space group $P2_12_12_1$. The data of the unit cell are Z=4, a=8.18650(10) Å, b=9.97420(10) Å, c=32.8707(2) Å, α=β=γ=90.00°, cell volume=2684.02(5) Å$^3$, molecular formula=$C_{27}H_{25}N_9O_2$.2 $H_2O$, calculated density ρ=1.345 Mgm$^{-3}$ (at 20° C.).

Differential Scanning Calorimetry (DSC)

DSC measurements were performed with a METTLER DSC822e instrument. 40 μl Al-crucibles with sealed lid and hole were used and the measurements carried out in a nitrogen gas flow of 50 ml/min with a typical heating rate of 10° C./min, unless stated otherwise. The measured data were evaluated with the software STARe V8.10. For polymorph 1 of compound I, a DSC melting point with an onset temperature of 253° C. and a peak temperature of 257° C. was observed. In the DSC analysis of polymorph 2 of compound I, an endothermic peak with an onset temperature of 222° C. and a peak temperature of 225° C., followed by an endothermic peak with an onset temperature of 248° C. and a peak temperature of 251° C. was observed. The DSC behavior of hydrates 1 and 2 of compound I is described above.

Thermogravimetry (TG)

Thermogravimetric analyses were performed with a METTLER TGA851e instrument. 100 μl Al-crucibles with sealed lid and hole were used and the measurements performed in a nitrogen gas flow of 50 ml/min. The measured data were evaluated with the software STARe V8.10. TG measurements with infra-red (IR) spectroscopic analysis of volatiles were performed with a METTLER TGA851e instrument as described, which was coupled to a Thermo-Nicolet 380 FT-IR spectrometer equipped with a cell for gas phase measurements. The measured IR spectra were evaluated using the software OMNIC V.7.3. In the TG analyses of polymorph 1 and polymorph 2 of compound I until the melting point, insignificant weight losses of 0.2% and 0.7%, respectively, were observed. In the TG analysis of hydrate 1 of compound I, a gradual weight loss of 6.4% was observed between room temperature and 120° C. FT-IR analysis of the evolved gas proved it to be water. The observed weight loss corresponds to about 1.9 mol of water per mol of 2-(2-methylamino-pyrimidin-4-yl)-1H-indole-5-carboxylic acid [(S)-1-carbamoyl-2-(phenyl-pyrimidin-2-yl-amino)-ethyl]-amide. In the TG FT-IR analysis of hydrate 2 of compound I, a weight loss of 17-18% of water mainly in two steps was observed between room temperature and 140° C., which corresponds to about 6 mol of water per mol of 2-(2-methylamino-pyrimidin-4-yl)-

1H-indole-5-carboxylic acid [(S)-1-carbamoyl-2-(phenyl-pyrimidin-2-yl-amino)-ethyl]-amide.

Dynamic Vapor Sorption (DVS)

For the determination of the hygroscopicity, moisture sorption/desorption isotherms were recorded on a Surface Measurement Systems DVS-1 instrument. Two cycles were run at 25° C., in which the relative humidity was stepwise increased from 0% to 95% and subsequently decreased again to 0%, and the weight of the sample measured. The data were evaluated with the software DVSWin V.2.15. In the DVS analysis of polymorph 1 and polymorph 2 of compound I, in the sorption steps of the two cycles the following weight increases were observed.

| Relative humidity | Polymorph 1 | Polymorph 2 |
|---|---|---|
| 40% | 0.5%/0.5% | 0.2%/0.0% |
| 60% | 0.6%/0.6% | 0.3%/0.1% |
| 80% | 0.9%/0.9% | 0.4%/0.3% |
| 95% | 1.3%/1.4% | 0.8%/0.6% |

Determination of Solubility

For the determination of the solubility in a mixture of acetone and water (4:1, by volume), samples of 0.5 mg to 50 mg of the test substances were suspended in a defined amount of the solvent (800 mg to 1200 mg) in screw cap vials with a magnetic stirring bar, which were placed in a temperature-controlled multiple stirring device equipped for transmission measurement (Avantium Crystal 16). With stirring at 700 rpm, the vials were cooled from room temperature to 0° C. and then heated to 60° C. with a heating rate of 3° C./h, kept at 60° C. for 2 h and cooled again to 0° C. with a cooling rate of 3° C./h. By means of transmission measurement it was determined whether the sample was dissolved (100% transmission), or crystals were present. For polymorph 1, polymorph 2, hydrate 1 and hydrate 2 of compound I the following solubilities in a mixture of acetone and water (4:1, by volume) were determined.

| Substance | Temperature | Solubility [g in 100 g of solvent] |
|---|---|---|
| Polymorph 1 | 36.9° C. | 0.43 |
| Polymorph 1 | 44.7° C. | 0.50 |
| Polymorph 1 | 60.0° C. | 0.85 |
| Polymorph 2 | 46.0° C. | 1.02 |
| Polymorph 2 | 57.5° C. | 2.48 |
| Hydrate 1 | 38.6° C. | 2.11 |
| Hydrate 1 | 49.7° C. | 3.39 |
| Hydrate 1 | 57.4° C. | 5.04 |
| Hydrate 2 | 36.8° C. | 0.50 |
| Hydrate 2 | 46.1° C. | 1.02 |
| Hydrate 2 | 55.9° C. | 2.61 |

Maturation Experiments

By maturation experiments (slurry conversion) at 20° C. the relative stability of polymorphs 1 and 2 and hydrate 1 was investigated.

A polymorph mixture of 81 mg (Mixture of Polymorph 1 and Polymorph 2), 83 mg of Polymorph 1 and 60 mg of hydrate 1 was prepared. The mixture was subjected to XRPD analysis to confirm the presence of all three polymorphs and then distributed into five capillaries. These samples were kept in suspension at 20° C. for five days. After X-ray powder diffraction measurement of the suspensions these were dried over night at 40° C. and <100 mbar and again subjected to X-ray diffraction. Maturation experiments (a) to (e) were performed under the specified conditions, starting with the polymorph mixture described above.

(a) The polymorph mixture was suspended in water. After stirring the suspension for five days at 20° C., the suspension was analyzed via XRPD and a mixture of polymorph 1 and hydrate 1 was proven. After drying over night at 40° C. and <100 mbar the obtained solid was analyzed via XRPD, again, and only polymorph 1 was found.

(b) The polymorph mixture was suspended in water/methanol 1:1 (vol.:vol.). After stirring the suspension for five days at 20° C., the suspension was analyzed via XRPD and only polymorph 1 was proven. After drying over night at 40° C. and <100 mbar the obtained solid was analyzed via XRPD, again, and only polymorph 1 was found.

(c) The polymorph mixture was suspended in 2-propanol. After stirring the suspension for five days at 20° C., the suspension was analyzed via XRPD and only polymorph 1 was proven. After drying over night at 40° C. and <100 mbar the obtained solid was analyzed via XRPD, again, and only polymorph 1 was found.

(d) The polymorph mixture was suspended in acetone. After stirring the suspension for five days at 20° C., the suspension was analyzed via XRPD and only polymorph 1 was proven. After drying over night at 40° C. and <100 mbar the obtained solid was analyzed via XRPD, again, and only polymorph 1 was found.

(e) The polymorph mixture was suspended in ethylacetate. After stirring the suspension for five days at 20° C., the suspension was analyzed via XRPD and only polymorph 1 was proven. After drying over night at 40° C. and <100 mbar the obtained solid was analyzed via XRPD, again, and only polymorph 1 was found.

In all maturation experiments (a) to (e) the solid completely transformed to polymorph 1 after drying. The performed maturation experiments prove that polymorph 1 is thermodynamically most stable among polymorphs 1, 2 and hydrate 1.

The invention claimed is:

1. A crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide, which is selected from the group consisting of polymorph 1, polymorph 2, polymorph 3, hydrate 1 and hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide and mixture thereof.

2. Polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, which has characteristic reflections in an X-ray powder diffractogram using CuK-alpha1 radiation in reflection mode at 2Theta angles (in degree) of 14.9±0.2, 19.4±0.2, 19.7±0.2, 20.0±0.2, 22.3±0.2, 25.0±0.2.

3. Polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, which has characteristic reflections in an X-ray powder diffractogram using CuK-alpha1 radiation in reflection mode at 2Theta angles (in degree) of 5.8±0.2, 6.7±0.2, 9.3±0.2, 11.2±0.2, 19.4±0.2, 22.1±0.2.

4. Polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, which has characteristic reflections in an X-ray powder diffractogram using CuK-alpha1 radiation in reflection mode at 2Theta angles (in degree) of 15.2±0.2, 15.9±0.2, 17.3±0.2, 19.2±0.2, 22.2±0.2, 25.3±0.2.

5. Hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, which has characteristic reflections in an X-ray powder diffractogram using CuK-alpha1 radiation in reflection mode at 2Theta angles (in degree) of 5.3±0.2, 13.5±0.2, 17.9±0.2, 19.5±0.2, 21.5±0.2, 24.9±0.2.

6. Hydrate 2 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, which has characteristic reflections in an X-ray powder diffractogram using CuK-alpha1 radiation in reflection mode at 2Theta angles (in degree) of 2.9±0.2, 5.3±0.2, 8.3±0.2, 11.5±0.2, 17.1±0.2, 22.8±0.2.

7. A pharmaceutical composition comprising at least one of polymorphs 1, 2 and 3 and hydrates 1 and 2 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, and one or more pharmaceutically acceptable excipients.

8. A pharmaceutical composition comprising polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 2 and one or more pharmaceutically acceptable excipients.

9. A method for treating a disease selected from rheumatoid arthritis, osteoarthritis, inflammatory bowel disease, a disease which is due to overexpression of tumor necrosis factor alpha (TNFα) or an increased concentration of TNFα selected from Crohn's disease and intestinal ulcers, and treatment of an acute or chronic rejection reaction on the part of the organ recipient against the transplanted organ, comprising administering to such patient a pharmaceutically effective amount of the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1.

10. The method of claim 9, wherein the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide is polymorph 1 having characteristic reflections in an X-ray powder diffractogram using CuK-alpha1 radiation in reflection mode at 2Theta angles (in degree) of 14.9 ±0.2, 19.4 ±0.2, 19.7 ±0.2, 20.0 ±0.2, 22.3 ±0.2, 25.0 ±0.2.

11. A process for preparing polymorph 3 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, comprising drying hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK-alpha1 radiation in reflection mode at 2Theta angles (in degree) of 5.3±0.2, 13.5±0.2, 17.9±0.2, 19.5±0.2, 21.5±0.2, 24.9±0.2, at a temperature of 50 to 70° C. and a pressure of 20 to 50 mbar.

12. A process for preparing a crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1, comprising:
heating a polymorph or hydrate of 2-(2-methylamino-pyrimidin-4-yl)-1H-indole-5-carboxylic acid [(S)-1-carbamoyl-2-(phenyl-pyrimidin-2-yl-amino)-ethyl]-amide in a solvent to a temperature of about 50° C. to about 70° C.; and
cooling the mixture to 20° C. to 25° C.

13. A process for preparing polymorph 1 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 12, comprising:
heating polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK-alpha1 radiation in reflection mode at 2Theta angles (in degree) of 5.8±0.2, 6.7±0.2, 9.3±0.2, 11.2±0.2, 19.4±0.2, 22.1±0.2, in a mixture of acetone and water at a temperature of about 50° C. to about 60° C.

14. A process for preparing polymorph 2 of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 12, comprising:
heating hydrate 1 of 2-(2-methylamino-pyrimidin-4-yl)-1H-indole-5-carboxylic acid [(S)-1-carbamoyl-2-(phenyl-pyrimidin-2-yl-amino)-ethyl]-amide which has characteristic reflections in an X-ray powder diffractogram using CuK-alpha1 radiation in reflection mode at 2Theta angles (in degree) of 5.3±0.2, 13.5±0.2, 17.9±0.2, 19.5±0.2, 21.5±0.2, 24.9±0.2, in a mixture of diisopropyl ether and methanol to a temperature of about 60° C. to about 70° C.

15. A method for treating chronic pain in a patient in need thereof, comprising administering to such patient a pharmaceutically effective amount of the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide according to claim 1.

16. The method of claim 15, wherein the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide is polymorph 1 having characteristic reflections in an X-ray powder diffractogram using CuK-alpha1 radiation in reflection mode at 2Theta angles (in degree) of 14.9 ±0.2, 19.4 ±0.2, 19.7 ±0.2, 20.0 ±0.2, 22.3 ±0.2, 25.0 ±0.2.

17. The method of claim 15, wherein the chronic pain is associated with chronic musculoskeletal disease, osteoarthritis, rheumatoid arthritis, intestinal inflammation, cardiac muscle inflammation, multiple sclerosis or neuritis.

18. The method of claim 17, wherein the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide is polymorph 1 having characteristic reflections in an X-ray powder diffractogram using CuK-alpha1 radiation in reflection mode at 2Theta angles (in degree) of 14.9 ±0.2, 19.4 ±0.2, 19.7 ±0.2, 20.0 ±0.2, 22.3 ±0.2, 25.0 ±0.2.

19. The method of claim 15, wherein the chronic pain is associated with osteoarthritis.

20. The method of claim 19, wherein the crystalline form of 2-(2-methylamino-pyrimidin-4-yl)-1H-indole-5-carboxylic acid [(S)-1-carbamoyl-2-(phenyl-pyrimidin-2-yl-amino)-ethyl]-amide is polymorph 1 having characteristic reflections in an X-ray powder diffractogram using CuK-alpha1 radiation in reflection mode at 2Theta angles (in degree) of 14.9 ±0.2, 19.4 ±0.2, 19.7 ±0.2, 20.0 ±0.2, 22.3 ±0.2, 25.0 ±0.2.

* * * * *